United States Patent [19]

Treuner

[11] 4,077,956
[45] Mar. 7, 1978

[54] 5-SUBSTITUTED DERIVATIVES OF DIPYRAZOLO[1,5a:4',3'-e]PYRAZINE-6-CARBOXYLIC ACIDS AND ESTERS

[75] Inventor: Uwe D. Treuner, Regensburg, Germany

[73] Assignee: E. R. Squibb & Sons, Inc., Princeton, N.J.

[21] Appl. No.: 718,748

[22] Filed: Aug. 30, 1976

[51] Int. Cl.$^2$ ............................................. C07D 487/14
[52] U.S. Cl. ..................... 260/250 BC; 260/268 TR; 544/107; 544/115
[58] Field of Search ................. 260/250 BC, 268 TR, 260/247.2 R, 247.2 B

[56] References Cited

U.S. PATENT DOCUMENTS 3,282,954  11/1966  Stein et al. ........................... 548/376

OTHER PUBLICATIONS

Ring Index entry 2362.
Chemical Abstracts, vol. 84, 1876cs.

Primary Examiner—Donald G. Daus
Assistant Examiner—Jose Tovar
Attorney, Agent, or Firm—Lawrence S. Levinson; Merle J. Smith

[57] ABSTRACT

New 5-substituted derivatives of dipyrazolo[1,5-a:4',3'-e]pyrazine-6-carboxylic acid, esters and their salts have the formula

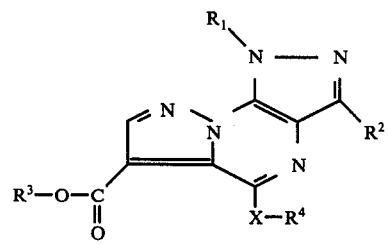

$R^1$ is hydrogen, lower alkyl or phenyl-lower alkylene; $R^2$ and $R^3$ each is hydrogen or lower alkyl; X is oxygen or sulfur; and $R^4$ is hydrogen, lower alkyl, phenyl-lower alkylene or amino-lower alkylene.

The new compounds are useful as anti-inflammatory agents and immunosuppressive agents.

13 Claims, No Drawings

5-SUBSTITUTED DERIVATIVES OF DIPYRAZOLO[1,5-a:4',3'-E]PYRAZINE-6-CARBOXYLIC ACIDS AND ESTERS

SUMMARY OF THE INVENTION

This invention relates to new 5-substituted derivatives of dipyrazolo[1,5-a:4',3'-e]pyrazine-6-carboxylic acids and esters which have the formula

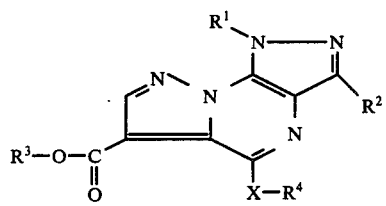

wherein $R^1$ is hydrogen, lower alkyl or phenyl-lower alkylene; $R^2$ and $R^3$ each is hydrogen or lower alkyl; $R^4$ is hydrogen, lower alkyl, phenyl-lower alkylene or an amino-lower alkylene group, i.e., -lower alkylene

wherein $R^5$ And $R^6$ each is hydrogen or lower alkyl or together with the nitrogen complete an unsubstituted or substituted pyrrolidino, piperidino, piperazinyl or morpholino group, the substituent on the heterocyclic being one or two lower alkyl groups; X is oxygen (—O—) or sulfur (—S—); and salts thereof.

The foregoing symbols have the same meaning throughout this specification.

DETAILED DESCRIPTION OF THE INVENTION

The various groups represented by the symbols are of the following kind:

The lower alkyl groups are straight or branched chain hydrocarbon groups having up to seven carbon atoms in the chain, e.g., methyl, ethyl, propyl, isopropyl, butyl, isobutyl, t-butyl, amyl, hexyl, heptyl, etc. The $C_1$-$C_4$ lower alkyl groups and especially $C_1$-$C_2$ groups are preferred.

The phenyl-lower alkylene groups have a phenyl group attached to an alkyl chain such as those described. The same carbon preferences apply, but especially preferred are phenylmethyl and phenylethyl.

The amino-lower alkylene groups referred to above are linked to the ring through an oxygen or sulfur atom. The group

is attached to an alkylene chain like those described above with the $C_2$-$C_4$ and $C_2$-$C_3$ alkylene chains constituting preferred and especially preferred groups, respectively. $R^5$ and $R^6$ each is hydrogen or lower alkyl or together with the nitrogen complete an unsubstituted or substituted heterocyclic of the group pyrrolidine, piperidine, piperazine or morpholine, each of which may bear one or two methyl groups. Such amino-lower alkylene groups include, for example, aminoethyl, aminopropyl, methylaminoethyl, methylaminopropyl, ethylaminoethyl, propylaminoethyl, isopropylaminoethyl, dimethylaminoethyl, dimethylaminopropyl, diethylaminoethyl, dipropylaminoethyl, methylethylaminoethyl, piperidinomethyl, piperidinoethyl, piperidinopropyl, pyrrolidinomethyl, pyrrolidinoethyl, piperazin-1-ylmethyl, 2-piperazin-1-ylethyl, morpholinomethyl, 2-morpholinoethyl, 4-methylpiperazin-1-ylmethyl, 4-hydroxyethylpiperazin-1-ylmethyl, 4-methylpiperidinomethyl, etc.

The products of the examples are preferred embodiments.

Especially preferred compounds of formula are those wherein $R^1$ and $R^2$ each is lower alkyl, especially methyl;

$R^3$ and $R^4$ is hydrogen or lower alkyl, especially hydrogen, methyl or ethyl;

X is oxygen or sulfur, especially oxygen.

The compounds of formula I are produced by the following sequence of reactions.

A 5-halopyrazole having the formula

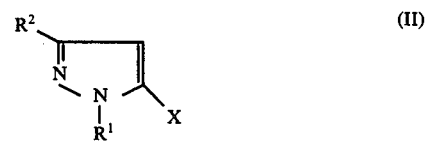

wherein $R^1$ and $R^2$ have the same meanings defined above and X is halogen, preferably chlorine or bromine especially chlorine, is nitrated with fuming nitric acid to form a nitro derivative of the formula

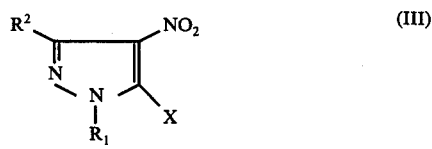

This nitro derivative is then made to react with hydrazine, e.g. in an alcohol like propanol at an elevated temperature about 100° C, to obtain a 5-hydrazino-4-nitro-1H-pyrazole of the formula

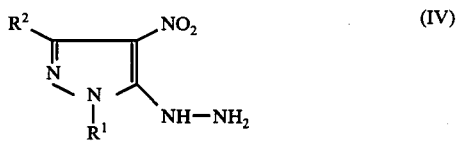

This 5-hydrazino-4-nitro-1H-pyrazole of formula IV is made to react with an alkoxymethyleneoxalacetic acid ester of the formula

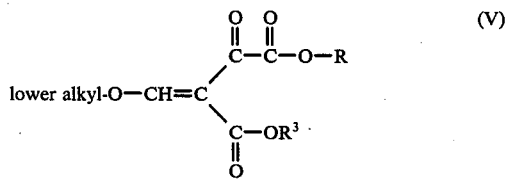

wherein R and $R^3$ each is lower alkyl, preferably ethyl, e.g., by heating at a temperature about reflux temperature in an alcohol like ethanol or acid like glacial acetic acid. The resulting compound of the formula

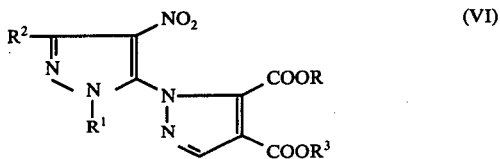

is hydrogenated in the presence of a catalyst like palladium on carbon in an acid like glacial acetic acid or an alcohol like ethanol or butanol, producing a compound of the formula

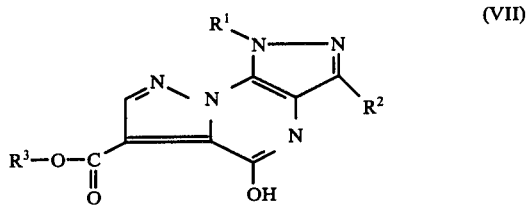

(or its keto form).

The intermediate of formula VII is halogenated with a halogenating agent, e.g., a phosphorus oxyhalide like phosphorus oxychloride in the presence of dimethylformamide, preferably at reflux temperature, to produce a compound of the formula

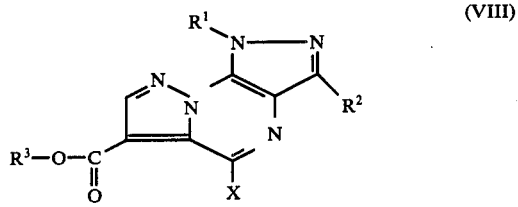

wherein X is halogen (preferably chlorine or bromine).

The compound of formula VIII is then made to react with a compound of the formula $$R^4XH \qquad IX$$

preferably a metal salt thereof like an alkali metal or alkaline earth metal salt. Such reactants include, for example an alkali metal alkoxide like sodium methoxide, potassium ethoxide or the like or an alkali metal salt of a mercaptan like sodium mercaptide, etc. The reaction is effected by heating at about reflux temperature in a solvent, e.g., an alcohol like ethanol to obtain a product of formula I wherein $R^3$ is lower alkyl.

This ester is converted to the acid ($R^3$=H) by conventional hydrolysis, e.g., with an equivalent of acid like hydrochloric acid or base like sodium or potassium hydroxide.

The acid group also forms salt with basic groups, e.g., metals, for example, alkali metals like sodium, alkaline earth metals like calcium and magnesium, or organic bases like pyridine, etc. $R_3$ can thus also be characterized as a salt forming ion. These salts can be produced from the ester, i.e., $R_3$ is lower alkyl, by reaction with an excess of base. The salts are useful for forming soluble derivatives, for purification purposes or as intermediates. They are also within the scope of the invention.

Additional experimental details are found in the examples.

The new compounds of this invention have anti-inflammatory properties and are useful for administration orally or parenterally as antiinflammatory agents, for example, to reduce local inflammatory conditions such as those of an edematous nature or resulting from proliferation of connective tissue in various mammalian species such as rats, dogs and the like when given orally or parenterally in dosages of about 2 to 50 mg/kg/day, preferably 5 to 25 mg/kg/day, in single or 2 to 4 divided doses, as indicated by the carageenan edema assay in rats or delayed hypersensitivity skin reaction test in rats.

The compounds of this invention also can be used as immunosuppressive agents, i.e., to suppress the immune response which is a defensive mechanism in animal species against foreign bodies. Thus they may be used, for example, in preventing rejection of organ transplants or skin grafts such as renal transplants or skin grafts as shown in dogs or mice or in suppressing the antibody response in mice to an injection of red blood cells of sheep. The compounds may be administered orally or parenterally, e.g., subcutaneously, in amounts of about 10 to 75 mg/kg daily in single doses or two to four divided doses.

The compounds of the invention can be utilized by formulating in compositions such as tablets, capsules or elixirs for oral administration or in sterile solutions or suspensions for parenteral administration. About 10 to 250 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can also be applied topically as antiinflammatory agents formulated in a conventional lotion, ointment, or cream containing about 0.1 to 3 percent by weight of a compound of formula I or its salt.

The following examples are illustrative of the invention and constitute preferred embodiments. They also serve as models for the preparation of other members of the group which can be produced by suitable substitution of starting materials. All temperatures are in degrees celsius.

EXAMPLE 1

(a) 5-Chloro-1,3-dimethyl-4-nitro-1H-pyrazole 148.0 gms. of 5-chloro-1,3-dimethylpyrazole are added to 530 ml. of concentrated sulfuric acid at 0° and 370 ml. of fuming nitric acid are added dropwise with stirring. The reaction mixture is then stirred at 0° for 4 hours, poured over 250 gms. of ice and extracted with methylene chloride. 138 gms. of the product, 5-chloro-1,3-dimethyl-4-nitro-1H-pyrazole, are obtained from the dried organic phase as white crystals, m.p. 77°-78°.

(b) 5-Hydrazino-1,3-dimethyl-4-nitro-1H-pyrazole 39 gms. of hydrazine are dissolved in 500 ml. of n-propanol and 105 gms. of 1,3-dimethyl-4-nitro-5-chloro-1H-pyrazole dissolved in propanol are added dropwise at 100°. The reaction mixture is then refluxed for 4 hours. On cooling, 5-hydrazino-1,3-dimethyl-4-nitro-1H-pyrazole crystallizes in the form of yellow needles. By concentrating the mother liquor an additional quantity of product is obtained. The combined crude is recrystallized from propanol, yield 98 gms. of yellow needles, m.p. 177°-179°.

(c)
1-(1,3-Dimethyl-4-nitro-1H-pyrazol-5-yl)-1H-pyrazole-4,5-dicarboxylic acid, diethyl ester 120 gms. of 5-hydrazino-1,3-dimethyl-4-nitro-1H-pyrazole are dissolved in 500 ml. of absolute ethanol and 173 gms. of ethoxymethylene oxalacetic acid ethyl ester dissolved in 300 ml. of ethanol are slowly added dropwise. After refluxing for 10 hours and distilling off the solvent, the product, 1-(1,3-dimethyl-4-nitro-1H-pyrazol-5-yl)-1H-pyrazole-4,5-dicarboxylic acid, diethyl ester, is obtained as a brown oil, which crystallizes on trituration with cold ether, yield 143 gms. after recrystallization from cyclohexane/benzene, yellow crystals, m.p. 70°–80°.

(d)
5-Hydroxy-1,3-dimethyl-1H-dipyrazolo[1,5-a:4',3'-e]pyrazine-6-carboxylic acid, ethyl ester 50 gms. of 1-(1,3-dimethyl-4-nitro-1H-pyrazol-5-yl)-1H-pyrazole-4,5-dicarboxylic acid, diethyl ester, are hydrogenated with 0.2 gms. of palladium-carbon in 100 ml. of glacial acetic acid at 60° until the uptake of hydrogen stops. On cooling, the product, 5-hydroxy-1,3-dimethyl-1H-dipyrazolo[1,5-a:4',3'-e]pyrazine-6-carboxylic acid, ethyl ester, crystallizes in the form of white filamentous needles. On evaporating the solvent, the product is recrystallized from dimethylformamide, yield 22 gms. of white needles, m.p. 246°–247°.

EXAMPLE 2

(a)
5-Chloro-1,3-dimethyl-1H-dipyrazolo[1,5-a:4',3'-e]pyrazine-6-carboxylic acid, ethyl ester 92.5 gms. of 5-hydroxy-1,3-dimethyl-1H-dipyrazolo[1,5-a:4',3'-e]pyrazine-6-carboxylic acid, ethyl ester, together with 300 ml. of phosphorus oxychloride and 3 ml. of dimethylformamide are refluxed for 5 hours. After distilling off the phosphorus oxychloride, the reaction mixture is poured onto ice and the crude 5-chloro-1,3-dimethyl-1H-dipyrazolo[1,5-a:4',3'-e]pyrazine-6-carboxylic acid ethyl ester, is filtered under suction, then recrystallized from acetone, yield 83 gms. of white crystals, m.p. 130°–132°.

(b)
5-Ethoxy-1,3-dimethyl-1H-dipyrazolo[1,5-a:4',3'-e]pyrazine-6-carboxylic acid, ethyl ester 5.86 gms. of 5-chloro-1,3-dimethyl-1H-dipyrazolo[1,5-a:4',3'-e]pyrazine-6-carboxylic acid, ethyl ester, in ethanol is refluxed with 20 mM of sodium ethylate for 30 minutes. Upon cooling, the product, 5-ethoxy-1,3-dimethyl-1H-dipyrazolo[1,5-a:4',3'-e]pyrazine-6-carboxylic acid, ethyl ester, crystallizes in the form of white needles. The product is recrystallized from n-propanol, yield 4.2 gms, m.p. 116°–118°.

EXAMPLE 3
1,3-Dimethyl-5-(methylthio)-1H-dipyrazolo[1,5-a:4',3'-e]-pyrazine-6-carboxylic acid, ethyl ester 2.93 gms. of 5-chloro-1,3-dimethyl-1H-dipyrazolo[1,5-a:4',3'-e]pyrazine-6-carboxylic acid, ethyl ester, and 0.70 gms. of sodium methylmercaptide in 20 ml. of dimethylformamide are heated at 80° for 2 hours. Upon cooling, 100 ml. of water are added with stirring and the yellow product, 1,3-dimethyl-5-(methylthio)-1H-dipyrazolo[1,5-a:4',3'-e]pyrazine-6-carboxylic acid, ethyl ester, is filtered under suction and recrystallized from ethanol to obtain 2.9 gms. of the product as yellow needles, m.p. 86°–87°.

EXAMPLE 4
1,3-Dimethyl-5-mercapto-1H-dipyrazolo[1,5-a:4',3'-e]pyrazine-6-carboxylic acid, ethyl ester 5.86 gms. of 5-chloro-1,3-dimethyl-1H-dipyrazolo[1,5-a:4',3'-e]pyrazine-6-carboxylic acid, ethyl ester, are refluxed with 2 gms. of sodium bisulfide and 50 ml. of n-propanol for 3 hours. On cooling, the product, 1,3-dimethyl-5-mercapto-1H-dipyrazolo[1,5-a:4',3'-e]pyrazine-6-carboxylic acid, ethyl ester, crystallizes in the form of yellow filamentous needles which are recrystallized from n-propanol, yield 4.76 gms., m.p. 189°–191°.

EXAMPLE 5
5-Hydroxy-1,3-dimethyl-1H-dipyrazolo[1,5-a:4',3'-e]pyrazine-6-carboxylic acid 2.75 gms. of 5-hydroxy-1,3-dimethyl-1H-dipyrazolo[1,5-a:4',3'-e]pyrazine-6-carboxylic acid, ethyl ester are suspended in 20 ml. of concentrated hydrochloric acid. On warming, a clear solution results from which the product, 5-hydroxy-1,3-dimethyl-1H-dipyrazolo[1,5-a:4',3'-e]pyrazine-6-carboxylic acid, precipitates after 40 minutes as a crystal-like mass. The product is purified by dissolving the precipitate in concentrated ammonia solution, treating with charcoal, reprecipitating with hydrochloric acid and recrystallizing from dimethylformamide, m.p. > 300°.

The following additional products are obtained, respectively, by the procedure of Example 2 by substituting for the sodium ethylate or by the procedure of Example 3 by substituting for the sodium methylmercaptide the sodium salt of the R⁴XH compound shown in the first column and, if desired using a differently substituted 5-chloro-4-nitro-1H-pyrazole in Example 1, part a. The free acids and salts (R³=H or Na or K) are obtained as in Example 5.

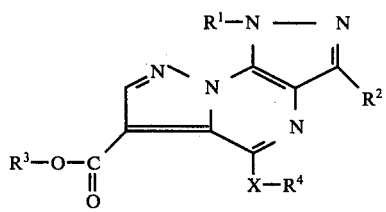

| Example | R⁴XH | R¹ | R² | R³ | R⁴X |
|---|---|---|---|---|---|
| 6 | C₂H₅OH | CH₃ | CH₃ | CH₃ | C₂H₅O— |
| 7 | C₄H₉OH | CH₃ | CH₃ | C₂H₅ | C₄H₉O— |

-continued

[Structure: pyrazolo-pyrimidine core with R¹-N—N, R², R³-O-C(=O), X-R⁴ substituents]

| Example | R⁴XH | R¹ | R² | R³ | R⁴X |
|---|---|---|---|---|---|
| 8 | phenyl-CH₂OH | $C_2H_5$ | H | $C_2H_5$ | phenyl-CH₂O— |
| 9 | $CH_3N$(piperazine)$NCH_2CH_2OH$ | $CH_3$ | $CH_3$ | $C_2H_5$ | $CH_3N$(piperazine)$N—CH_2CH_2O—$ |
| 10 | $(CH_3)_2NCH_2CH_2OH$ | H | $CH_3$ | $C_3H_7$ | $(CH_3)_2NCH_2CH_2O—$ |
| 11 | $NH_2CH_2CH_2OH$ | $C_2H_5$ | $C_2H_5$ | $C_2H_5$ | $NH_2CH_2CH_2O—$ |
| 12 | pyrrolidine-N-CH₂-CH(CH₂)-OH | H | H | $C_2H_5$ | pyrrolidine-N-CH₂-CH(CH₂)-O— |
| 13 | HN(piperazine)N-CH₂CH₂CH₂OH | $CH_3$ | H | $CH_3$ | HN(piperazine)N-CH₂CH₂CH₂O— |
| 14 | 4-CH₃-piperidine-NCH₂CH₂OH | $CH_3$ | $CH_3$ | $C_2H_5$ | 4-CH₃-piperidine-NCH₂CH₂O— |
| 15 | 3,5-di-CH₃-piperidine-NCH₂CH₂OH | H | H | $C_2H_5$ | 3,5-di-CH₃-piperidine-NCH₂CH₂O— |
| 16 | phenyl-CH₂CH₂OH | H | $C_2H_5$ | Na | phenyl-CH₂CH₂O— |
| 17 | phenyl-CH₂SH | $C_3H_7$ | H | $C_4H_9$ | phenyl-CH₂S— |
| 18 | phenyl-CH₂CH₂SH | H | $C_3H_7$ | $C_2H_5$ | phenyl-CH₂CH₂S— |
| 19 | $C_4H_9SH$ | $CH_3$ | $CH_3$ | $C_2H_5$ | $C_4H_9S—$ |
| 20 | $C_3H_7SH$ | $C_3H_7$ | $CH_3$ | $CH_3$ | $C_3H_7S—$ |
| 21 | $C_2H_5$ | $CH_3$ | $CH_3$ | $C_2H_5$ | $C_2H_5S—$ |
| 22 | $C_5H_{11}CHOH$ \| $CH_3$ | H | $C_4H_9$ | $C_2H_5$ | $C_5H_{11}CHO—$ \| $CH_3$ |
| 23 | $(CH_3)_2CHOH$ | $CH_3$ | $CH_3$ | H | $(CH_3)_2CHO—$ |
| 24 | $CH_3N$(piperazine)$NCH_2CH_2OH$ | H | —CH₂-phenyl | H | $CH_3—N$(piperazine)$NCH_2CH_2O—$ |
| 25 | $(CH_3)_2N(CH_2)_3OH$ | $CH_3$ | $CH_3$ | $C_2H_5$ | $(CH_3)_2N(CH_2)_3—O—$ |
| 26 | $(C_4H_9)_2NCH_2CH_2OH$ | $CH_3$ | —CH₂CH₂-phenyl | $CH_3$ | H | $(C_4H_9)_2NCH_2CH_2O—$ |
| 27 | morpholine-NCH₂CH₂OH | $CH_3$ | $CH_3$ | H | morpholine-NCH₂CH₂O— |
| 28 | $CH_3(CH_2)_4CHOH$ \| $CH_3$ | $C_2H_5$ | H | H | $CH_3(CH_2)_4CHO—$ \| $CH_3$ |

-continued

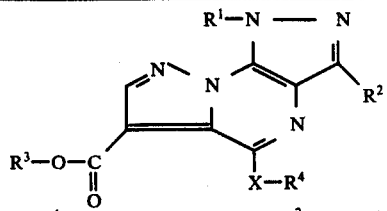

| Example | R⁴XH | R¹ | R² | R³ | R⁴X |
|---|---|---|---|---|---|
| 29 | ⌬N—(CH₂)₃OH | C₂H₅ | CH₃ | CH₃ | ⌬N—(CH₂)₃O— |
| 30 | H₂NCH₂CH₂SH | CH₃ | CH₃ | H | H₂NCH₂CH₂S— |
| 31 | CH₃NHCH₂OH | CH₃ | CH₃ | C₂H₅ | CH₃NCH₂O— |
| 32 | C₂H₅NHCH₂CH₂SH | CH₃ | CH₃ | C₂H₅ | C₂H₅NCH₂CH₂S— |
| 33 | NaSH | CH₃ | CH₃ | H | HS— |

What is claimed is:

1. A compound of the formula

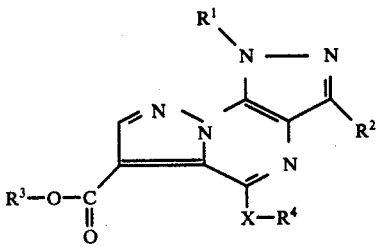

wherein
R¹ is hydrogen, lower alkyl or phenyl-lower alkylene;
R² and R³ each is hydrogen or lower alkyl; R⁴ is hydrogen lower alkyl, phenyl-lower alkylene or

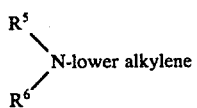

wherein R⁵ and R⁶ each is hydrogen or lower alkyl or together with the nitrogen complete one of the heterocyclics pyrrolidino, piperidino, morpholino or piperazinyl;
X is oxygen or sulfur; and salts thereof.

2. A compound as in claim 1 wherein X is oxygen.
3. A compound as in claim 1 wherein X is sulfur.
4. A compound as in claim 1 wherein R¹, R², R³ and R⁴ each is hydrogen or lower alkyl and X is sulfur or oxygen.
5. A compound as in claim 1 wherein R¹ and R² each is lower alkyl; R³ and R⁴ each is hydrogen or lower alkyl; and X is oxygen or sulfur.
6. A compound as in claim 1 wherein R¹ and R² each is methyl and R³ is ethyl.
7. A compound as in claim 6 wherein R⁴ is ethyl and X is oxygen.
8. A compound as in claim 6 wherein R⁴ is methyl and X is sulfur.
9. A compound as in claim 6 wherein R⁴ is hydrogen and X is sulfur.
10. A compound as in claim 6 wherein R⁴ is hydrogen and X is oxygen.
11. A compound as in claim 1 wherein R¹ and R² each is methyl; and R³ is hydrogen.
12. A compound as in claim 11 wherein R⁴ is hydrogen and X is oxygen.
13. A compound as in claim 11 wherein R⁴ is hydrogen and X is sulfur.

* * * * *

UNITED STATES PATENT AND TRADEMARK OFFICE
CERTIFICATE OF CORRECTION

PATENT NO. : 4,077,956
DATED : March 7, 1978
INVENTOR(S) : Uwe D. Treuner

It is certified that error appears in the above-identified patent and that said Letters Patent are hereby corrected as shown below:

Column 5, line 15 "70°" should read -- 79° --
Column 7, Example 21 under $R^4XH$ "$C_2H_5$" should read --$C_2H_5SH$--

Signed and Sealed this

Twelfth Day of June 1979

[SEAL]

Attest:

RUTH C. MASON
*Attesting Officer*

DONALD W. BANNER
*Commissioner of Patents and Trademarks*